US00PP13623P3

(12) United States Plant Patent
van Gaalen

(10) Patent No.: US PP13,623 P3
(45) Date of Patent: Mar. 4, 2003

(54) PHLOX PLANT NAMED 'NATURAL FEELINGS'

(76) Inventor: Irenaeus A. M. van Gaalen, Noordhoornseweg 37, 2635 GC Den Hoorn (NL)

( * ) Notice: Subject to any disclaimer, the term of this patent is extended or adjusted under 35 U.S.C. 154(b) by 0 days.

(21) Appl. No.: 09/984,538

(22) Filed: Oct. 30, 2001

(65) Prior Publication Data

US 2002/0112270 P1 Aug. 15, 2002

(51) Int. Cl.[7] ..... A01H 5/00

(52) U.S. Cl. ..... Plt./320

(58) Field of Search ..... Plt./320

*Primary Examiner*—Bruce R. Campell
*Assistant Examiner*—Annette H. Para
(74) *Attorney, Agent, or Firm*—Foley & Lardner

(57) ABSTRACT

A new and distinct cultivar of Phlox plant named 'Natural Feelings', characterized by its upright plant habit; inflorescence that does not shed but are persistent. inflorescences do not have typical Phlox flowers; green leaf color, many flowers per stem and light greyed-purple; red-purple; flowers with white and yellow-green tips.

3 Drawing Sheets

LATIN NAME OF THE GENUS AND SPECIES OF THE PLANT CLAIMED

*Phlox paniculata.*

VARIETY DENOMINATION

'Natural Feelings'.

BACKGROUND OF THE INVENTION

The present invention relates to a new and distinct cultivar of Phlox plant of the family Polemoniaceae, botanically known as *Phlox paniculata*, and hereinafter referred to by the cultivar name 'Natural Feelings'.

The new cultivar is a whole plant mutation from Phlox 'Bright Eye Elite' (unpatented) in Den Hoorn, The Netherlands. 'Natural Feelings' was discovered and selected by the inventor, Irenaeus A. M. van Gaalen, in September 2000, in Den Hoorn, The Netherlands.

'Natural Feelings' is a product of a planned breeding program conducted by the Inventor and selected in a cultivated environment in Den Hoorn, The Netherlands. Asexual reproduction of the new cultivar by tissue culture was first performed in September 2000 in Maasdijk, The Netherlands. Asexual reproduction of the new cultivar by cuttings (tip cutting, internodal cutting) was first performed June, 2001, in Den Hoorn, The Netherlands and has demonstrated that the combination of characteristics as herein disclosed for the new cultivar are firmly fixed and reproduce true to type in successive generations of asexual reproduction.

BRIEF DESCRIPTION OF THE INVENTION

The following traits have been repeatedly observed and are determined to be basic characteristics of 'Natural Feelings' which in combination distinguish this Phlox as a new and distinct cultivar:

1. Inflorescences atypical of Phlox flowers;
2. Persistent inflorescences that do not shed;
3. Upright plant habit;
4. Green leaf color;

5. Many flowers per stem;
6. Light greyed-purple; red-purple; flowers with white and yellow-green tips.

'Natural Feelings' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Den Hoorn, The Netherlands, in a glass greenhouse under average day temperatures of between 18 to 32 degrees Celsius and 10 to 18 degrees Celcius at night. No artificial lighting, photoperiodic treatments or other cultural or environmental treatments are conducted, no growth retardants are added. These conditions closely approximate those generally used in commercial practice.

Of the many commercial cultivars known to the present inventor, the most similar in comparison to 'Natural Feelings' is the cultivar 'Red Feelings' (U.S. Plant patent application Ser. No. 09/984,576). In comparison, flowers of 'Natural Feelings' are green/white/pink whereas the flowers of 'Red Feelings' are reddish purple. The flower shape of 'Natural Feelings' resembles that of a small flower whereas the flower shape of 'Red Feelings' are less developed than a small flower. The inflorescences of 'Natural Feelings' have more flowers than the inflorescences of 'Red Feelings'.

In comparison to *Phlox paniculata* 'Bright Eye Elite', (unpatented) from which 'Natural Feelings' is a mutant, *Phlox paniculata* 'Bright Eye Elite' has normal *Phlox paniculata* flowers, whereas 'Natural Feelings' has much smaller flowers with different colors. 'Bright Eye Elite' has dark pink to light pink flowers that are 3.5 cm to 4 cm in length. The flowers of 'Natural Feelings' are green/white/pink in color and are 2 cm in length. The flowers of 'Natural Feelings' do not have reproductive organs contrary to the flowers of 'Red Feelings'. Generally, the stem, leaves and roots of 'Bright Eye Elite' and 'Natural Feelings' are the same.

BRIEF DESCRIPTION OF THE DRAWING

The accompanying photographic drawings show typical flower and foliage characteristics of 10 week old plants of 'Natural Feelings' with colors being as true as possible with illustrations of this type.

The first drawing shows a close-up of the inflorescence of 'Natural Feelings'.

The second drawing shows the inflorescence of 'Natural Feelings'.

The third drawing shows the new cultivar, 'Natural Feelings' in its entirety.

DETAILED BOTANICAL DESCRIPTION

The following observations, measurements and values describe the new cultivar at 24 months of age as grown in Den Hoorn, The Netherlands, in August, under conditions which closely approximate those generally used in commercial practice.

Color references are made to The Royal Horticultural Society Colour Chart (R.H.S), except where general colors of ordinary significance are used. Color values were taken under daylight conditions at approximately noon in Boskoop, The Netherlands.

Progagation:
- *Type cutting.*—Tissue cutting.

Plant:
- *General appearance and form.*—Herbaceous perennial, conical in shape.
- *Height.*—Average 80 cm.
- *Width.*—Average 50 cm.
- *Growth habit.*—Upright.
- *Winter hardiness.*—The lowest temperature tolerance is unknown but at least hardy to USDA Zone 6.
- *Plant vigor.*—Moderate, in spring approximately 15 cm per month (depending on temperature, moisture, etc).
- *Rooting habit.*—Freely branching.
- *Blooming habit.*—Once a year, continuously, on average four harvestable stems per year (young plant).
- *Blooming period.*—Summer, June–August.

Branching habit: Moderate; main shoots appear from base, the panicles are branched.
- *Number of lateral branches.*—Only the panicles are branched, average 10.
- *Lateral branch length.*—Average 5 cm.
- *Lateral branch diameter.*—Average 1.5 mm.

Stem:
- *Appearance/shape.*—Rounded, glabrous, slightly shiny.
- *Aspect.*—Circular.
- *Strength.*—Strong.
- *Internode length.*—6 cm on average.
- *Color.*—Green; RHS 143 A.
- *Pubescence.*—None.

Foliage:
- *Arrangement.*—Opposite.
- *Type.*—Single.
- *Color.*—Young leaves: Upper side green RHS 137 B to RHS 137 C; under side green RHS 137 B. Mature leaves: Upper side green, RHS 137 A; under side green, RHS 138A to RHS 138 B.
- *Length.*—Average 11 cm.
- *Width.*—2.8 cm.
- *Shape.*—Elliptic to narrow elliptic.
- *Apex.*—Acute.
- *Base.*—Attenuate.
- *Margin.*—Entire.
- *Texture.*—Smooth and glabrous on both sides, no pubescence.
- *Venation pattern.*—Pinnate.
- *Quantity.*—Main branches have an average of 20 leaves (10 pairs).
- *Midrib color.*—Green, 143 C to RHS 144 A.

Petioles:
- *Color.*—Green, RHS 143 C.
- *Size.*—Average length is 1.5 mm, average width is 4 mm, average height is 3 mm.

Flowers:
- *Flower type and habit.*—Typical Phlox flowers do not develop. Panicles with numerous clusters of bract-like structures are present. Bract-like structures are persistent.
- *Form.*—Double, no reproductive organs.
- *Flower shape.*—Salverform.
- *Borne.*—Inflorescence form is panicle.
- *Height.*—Average 25 cm.
- *Width.*—Average 22 cm.
- *Flower arrangement.*—Terminal panicle.
- *Quantity.*—Average over 100 per lateral, flowering branch; on average over 100 flower buds per lateral, flowering branch; on average over 750 flowers per main stem; on average over 3000 flowers and buds per plant.
- *Petal count.*—5.
- *Petal color.*—When Opening: Upper side: Tube light greyed-purple, RHS 186 C to RHS 186 D; petals red-purple, RHS 64 B to RHS 67 B; with white and yellow -green, RHS 144 B to RHS 144 C tips. Underside: Tube light greyed-purple, RHS 186 C to RHS 186 D; petals red-purple, RHS 70 B to RHS 70 C, with white and yellow-green, RHS 144 B tips.
- *Fully opened.*—Upper side: Tube light greyed-purple, RHS186 C to RHS 186 D; petals red-purple, RHS 64 B to RHS 67 B, with white and yellow-green, RHS 144 B to RHS 144 C tips. Under side: Tube light greyed-purple,; RHS 186 C to RHS 186 D, petals red-purple, RHS 70 B to RHS 70 C, with white and yellow-green, RHS 144 B tips.

Petals:
- *Shape.*—Spathulate, with the lower half fused (tube).
- *Appearance.*—Dull, twisted.
- *Texture.*—Smooth.
- *Arrangement.*—Rotate.
- *Number.*—5.
- *Tube.*—Fused.
- *Margin.*—Entire.
- *Tip.*—Aristate.
- *Length.*—Average 1.8 cm.
- *Width.*—Average 5 mm.

Sepals:
- *Appearance.*—Smooth, dull.
- *Arrangement.*—Rotate.
- *Number.*—5.
- *Shape.*—Campanulate.
- *Margin.*—Entire.
- *Tip.*—Apiculate.
- *Base.*—Fused into a campanulate structure.
- *Length.*—Average 6 mm.
- *Width.*—Base of the tips on average 1 mm.

*Color.*—Immature: Upper side green, RHS 141 C to RHS 141 D; under side green, RHS 141 C to RHS 141 D. Mature: Upper side green, RHS 141 C darker towards the tips (RHS 141 A); under side green, RHS 141 B to RHS 141 C darker at tips (RHS 141 A).

*Flower size.*—Average 2 cm in length and 1.5 cm in diameter.

*Flower type.*—Double.

*Fragrance.*—None.

Roots: Thick, fibrous, in summer it takes about 20 days at 20 degrees Celsius to produce a rooted cutting; in winter it takes about 35 days at 12 degrees Celsius to produce; freely branching rooting habit.

Reproductive organs: The flowers have no reproductive organs.

Seeds: No fruits no seeds are developed.

Disease resistance/susceptibility: No observations made.

I claim:

1. A new and distinct Phlox plant named 'Natural Feelings', substantially as illustrated and described herein.

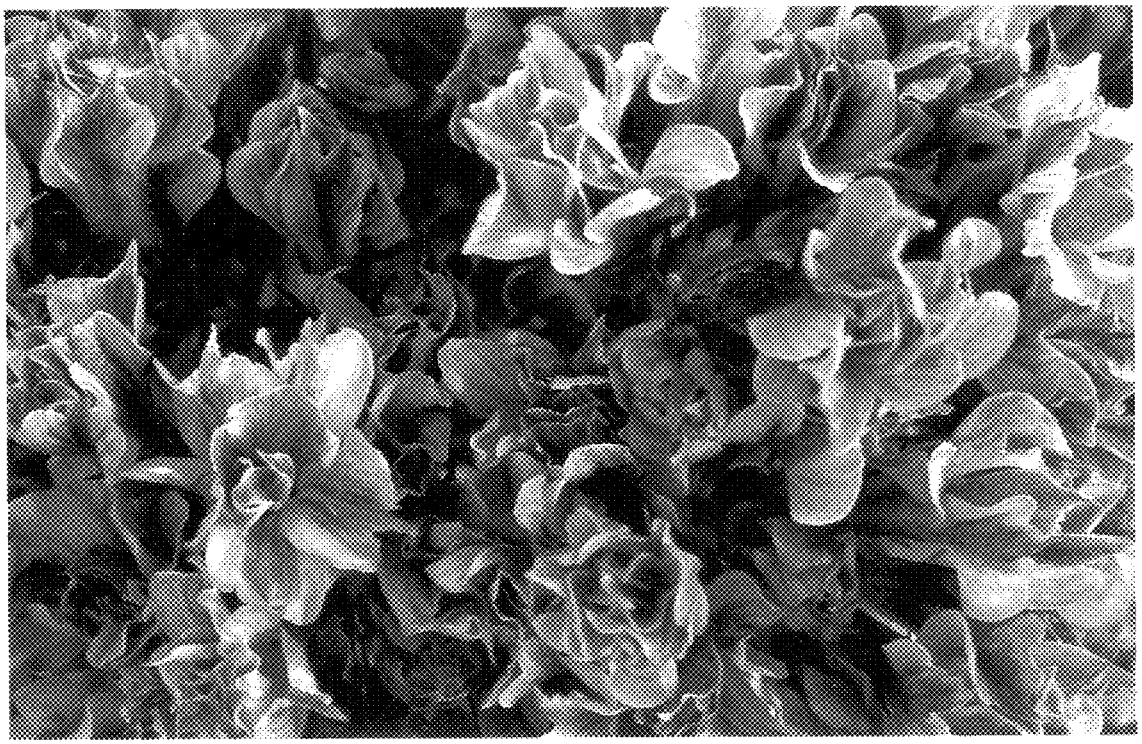

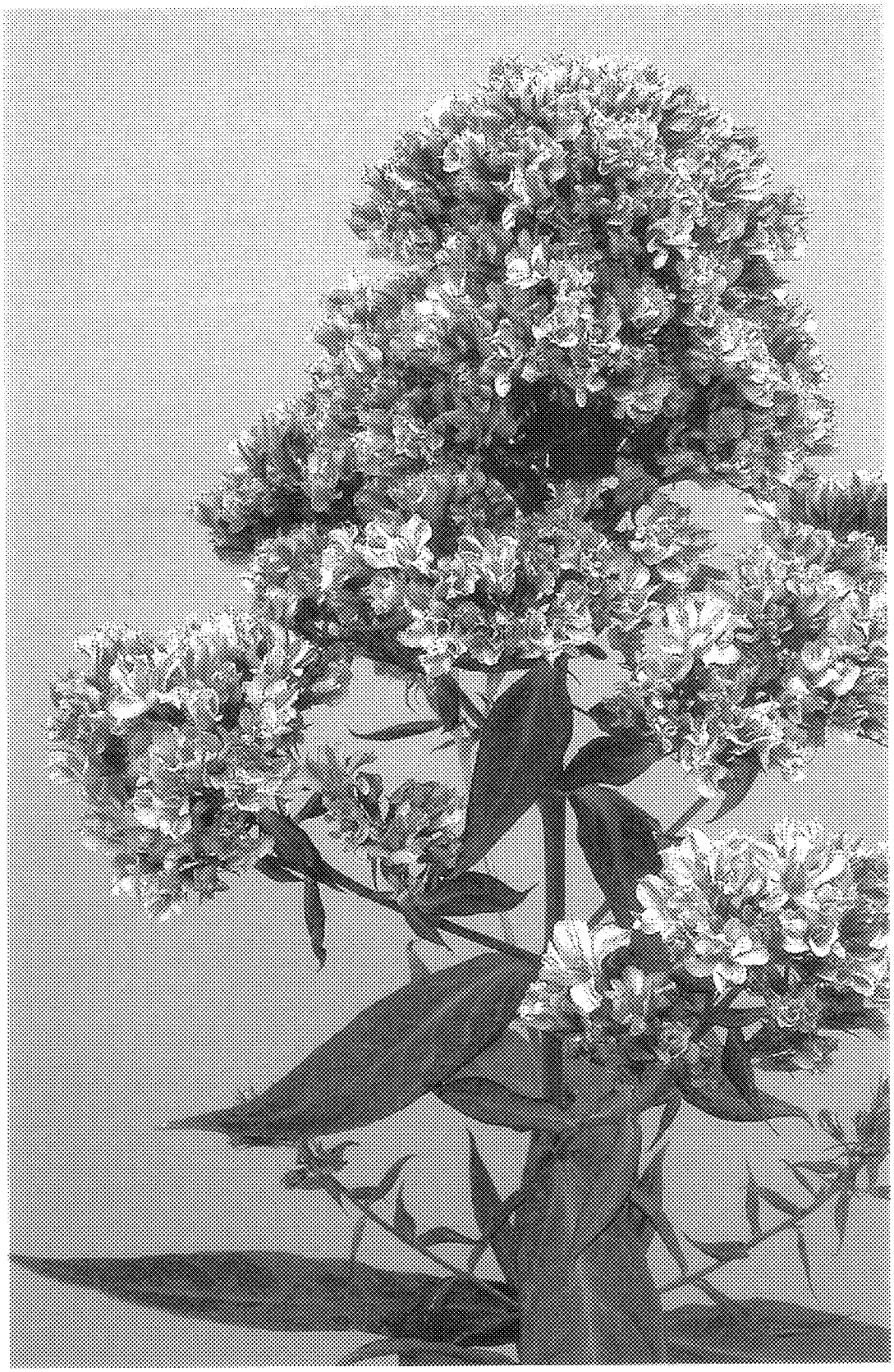

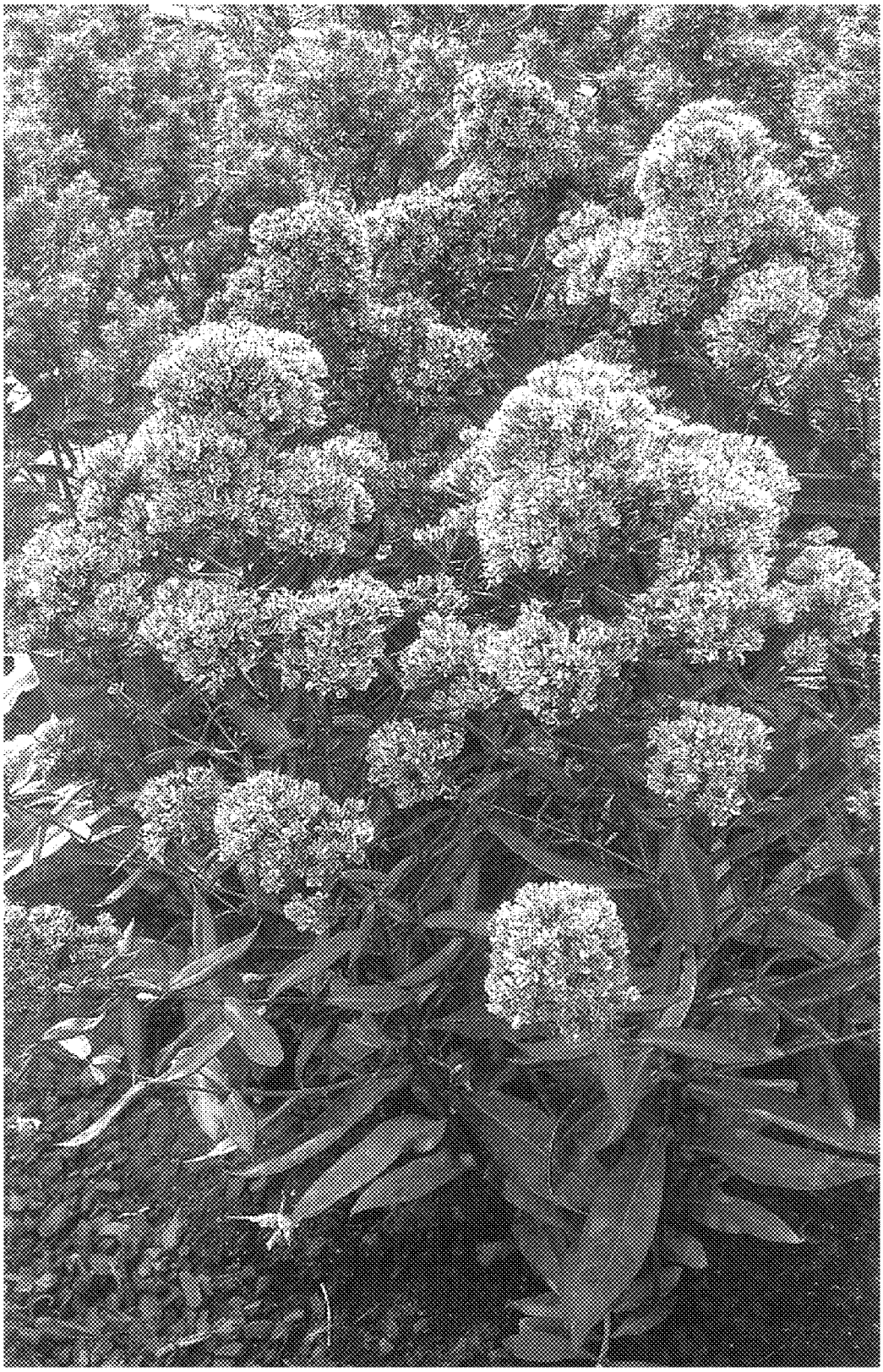

* * * * *